United States Patent
Johnson

(10) Patent No.: US 8,536,901 B2
(45) Date of Patent: Sep. 17, 2013

(54) WIRELESS BIO-INTERFACE DATA TRANSMISSION SYSTEM

(75) Inventor: Lee James Johnson, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 185 days.

(21) Appl. No.: 13/309,832

(22) Filed: Dec. 2, 2011

(65) Prior Publication Data
US 2012/0139613 A1 Jun. 7, 2012

Related U.S. Application Data

(60) Provisional application No. 61/419,000, filed on Dec. 2, 2010.

(51) Int. Cl.
*H03K 3/84* (2006.01)
(52) U.S. Cl.
USPC .......................................... 327/100
(58) Field of Classification Search
USPC ................................. 327/100, 415
See application file for complete search history.

(56) References Cited

U.S. PATENT DOCUMENTS 6,647,297 B2 11/2003 Scribner
7,365,577 B2 * 4/2008 Schneider et al. ............ 327/100

* cited by examiner

*Primary Examiner* — Hai L Nguyen
(74) *Attorney, Agent, or Firm* — Amy Ressing; Suresh Koshy

(57) ABSTRACT

A method and an apparatus to drive an analog signal into a sensory tissue. The apparatus includes an analog-to-digital converter converting an original analog signal to a digital signal at an analog-to-digital converter sample rate. The apparatus includes a digital transceiver communicating wirelessly with the analog-to-digital converter to receive the digital signal. The apparatus includes a digital data buffer receiving the digital signal from the digital transceiver. The apparatus includes a digital-to-analog converter communicating with the digital data buffer and converting the digital signal into a reconstructed analog signal at a digital-to-analog converter sample rate faster than the analog-to-digital converter sample rate, the analog signal comprising a plurality of intensity values. The apparatus includes a pixel clock matching the digital-to-analog converter sample rate. The apparatus includes a bio-interface array comprising a plurality of electrodes and operably proximate to the sensory tissue.

13 Claims, 5 Drawing Sheets

WIRELESS BIO-INTERFACE DATA TRANSMISSION SYSTEM

This application claims the benefit of U.S. Provisional Application 61/419,000 filed on Dec. 2, 2010.

BACKGROUND OF THE INVENTION

Current wireless transceivers for use with implanted bio-interface devices use individual wireless channels for each electrode or use digital multiplexers to distribute the data. One problem is that current bio-interface digital multiplexers require a digital address for each pixel which adds to the number of bits required to set a pixel to a certain voltage. For instance, a 256 pixel array would require an additional 8-bits. This increases the overhead and data rate requirements. One way to eliminate the digital multiplexer is to use a separate transceiver circuit for each electrode. This is a poor solution in that it drastically increases the power and space requirements once more than 10 electrodes are required. A better method is to use an analog multiplexer to reduce power consumption. The problem with this seemingly better method is that the speed requirements for digital to analog conversion are increased once only one digital-to-analog converter is used. A more significant problem is that the speed of the analog multiplexer must be faster to read on or off the array data. This would require a very fast wireless transceiver, and its resultant power requirements would be higher.

BRIEF SUMMARY OF THE INVENTION

An embodiment of the invention includes an apparatus to drive an analog signal into a sensory tissue. The apparatus includes an analog-to-digital converter converting an original analog signal to a digital signal at an analog-to-digital converter sample rate. The apparatus includes a digital transceiver communicating wirelessly with the analog-to-digital converter to receive the digital signal. The apparatus includes a digital data buffer receiving the digital signal from the digital transceiver. The apparatus includes a digital-to-analog converter communicating with the digital data buffer and converting the digital signal into a reconstructed analog signal at a digital-to-analog converter sample rate faster than the analog-to-digital converter sample rate, the analog signal comprising a plurality of intensity values. The apparatus includes a pixel clock matching the digital-to-analog converter sample rate. The apparatus includes a bio-interface array comprising a plurality of electrodes and operably proximate to the sensory tissue, the bio-interface array communicating with the digital-to-analog converter, the digital data buffer, and the pixel clock so as to clock the plurality of intensity values in the reconstructed analog signal from the digital-to-analog converter into the plurality of electrodes of the bio-interface array.

Optionally, the apparatus further includes a row clock, wherein the bio-interface array includes a plurality of bit rows, the bio-interface array communicating with the row clock so as to clock the plurality of intensity values in the reconstructed analog signal from the digital-to-analog converter and the digital data buffer into the plurality of electrodes of the bio-interface array by bit row.

Optionally, the apparatus further includes a microprocessor communicating with the pixel clock, the digital data buffer, and the bio-interface array so as to controllably drive the reconstructed analog signal into the sensory tissue. Optionally, the reconstructed analog signal further includes a biphasic pulse, the microprocessor controllably driving the reconstructed analog signal into the sensory tissue upon detection of the biphasic pulse.

Optionally, the bio-interface array comprises at least one of a bio-interface stimulation array and a bio-interface recording array.

An embodiment of the invention includes a method of driving an analog signal into a sensory tissue. An original analog signal is converted into a digital signal using an analog-to-digital converter at an analog-to-digital converter sample rate. The digital signal is wirelessly transmitted to a digital-to-analog converter via a digital transceiver. The digital signal is buffered in a digital data buffer. The digital signal is converted into a reconstructed analog signal using the digital-to-analog converter at a digital-to-analog converter sample rate faster than the analog-to-digital converter sample rate, the reconstructed analog signal comprising a plurality of intensity values. A pixel clock is matched to the digital-to-analog converter sample rate. The plurality of intensity values in the reconstructed analog signal from the digital data buffer is clocked into a bio-interface array comprising a plurality of electrodes and operably proximate to the sensory tissue.

Optionally, the bio-interface array comprises a plurality of bit rows, the bio-interface array communicating with a row clock, wherein the method further includes clocking the plurality of intensity values in the reconstructed analog signal from the digital-to-analog converter and the digital data buffer into the plurality of electrodes of the bio-interface array by bit row.

Optionally, the method further includes controllably driving the constructed analog signal into the sensory tissue using a microprocessor communicating with the buffer, the pixel clock, and the bio-interface array.

Optionally, the analog signal further comprises a biphasic pulse, the microprocessor controllably driving the reconstructed analog signal into the sensory tissue upon detection of the biphasic pulse.

Optionally, the sensory tissue includes an eye, an ear, or a prosthetic limb.

Optionally, the bio-interface array includes a bio-interface stimulation array and/or a bio-interface recording array.

Alternative embodiments of the invention include a method and system is disclosed for high speed wireless control and readout of bio-interface devices. Illustrative features of such alternative embodiments of the current invention include, for example, a digital transceiver, a digital data buffer, an internal voltage control circuit and/or an analog multiplexer.

One or more of the embodiments of the instant invention solve the problem of limited digital data rates for wireless transceivers which do not reach the required data rates for analog multiplexers. For example, a standard stimulation multiplexer such as described in U.S. Pat. No. 6,647,297, incorporated herein by reference, runs at a 1 to 5 MHz pixel clock. For an 8-bit value, this requires data rates of at least 8 Mbps, before control bits are included. This is faster than most low power transceivers, such as Bluetooth 2.1 chips, which typically run at 3 Mbps. Such embodiments of the instant invention allow for a slow wireless data clock and a faster multiplexer clock by buffering and then releasing the data will a higher clock speed matched to the multiplexer design.

In one or more embodiments of the instant invention, it is desirable to record from biological tissues, such as neuronal or cardiac tissues. This often requires very high speed to record simultaneously from the tissues. Such embodiments address the speed mismatch from recording to wireless transmission by using the same buffering approach described above. In addition, such embodiments of the invention optionally use on-chip processing to analyze the tissue signals prior to transmission to significantly reduce the amount of data transmitted.

DETAILED DESCRIPTION OF THE INVENTION

Figure 1:
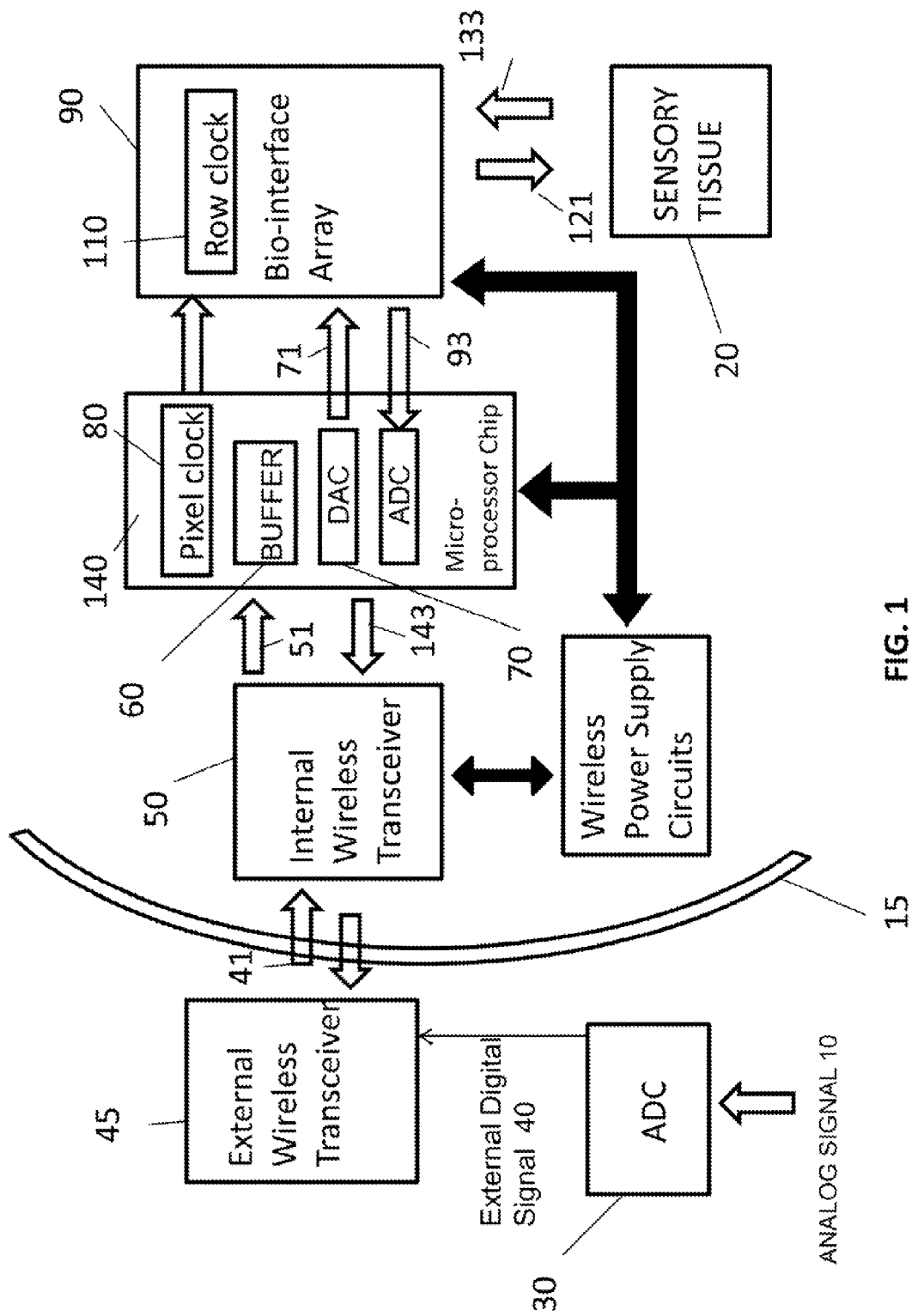
FIG. 1 is a block diagram of an illustrative apparatus embodiment according to the instant invention.
Figure 2:
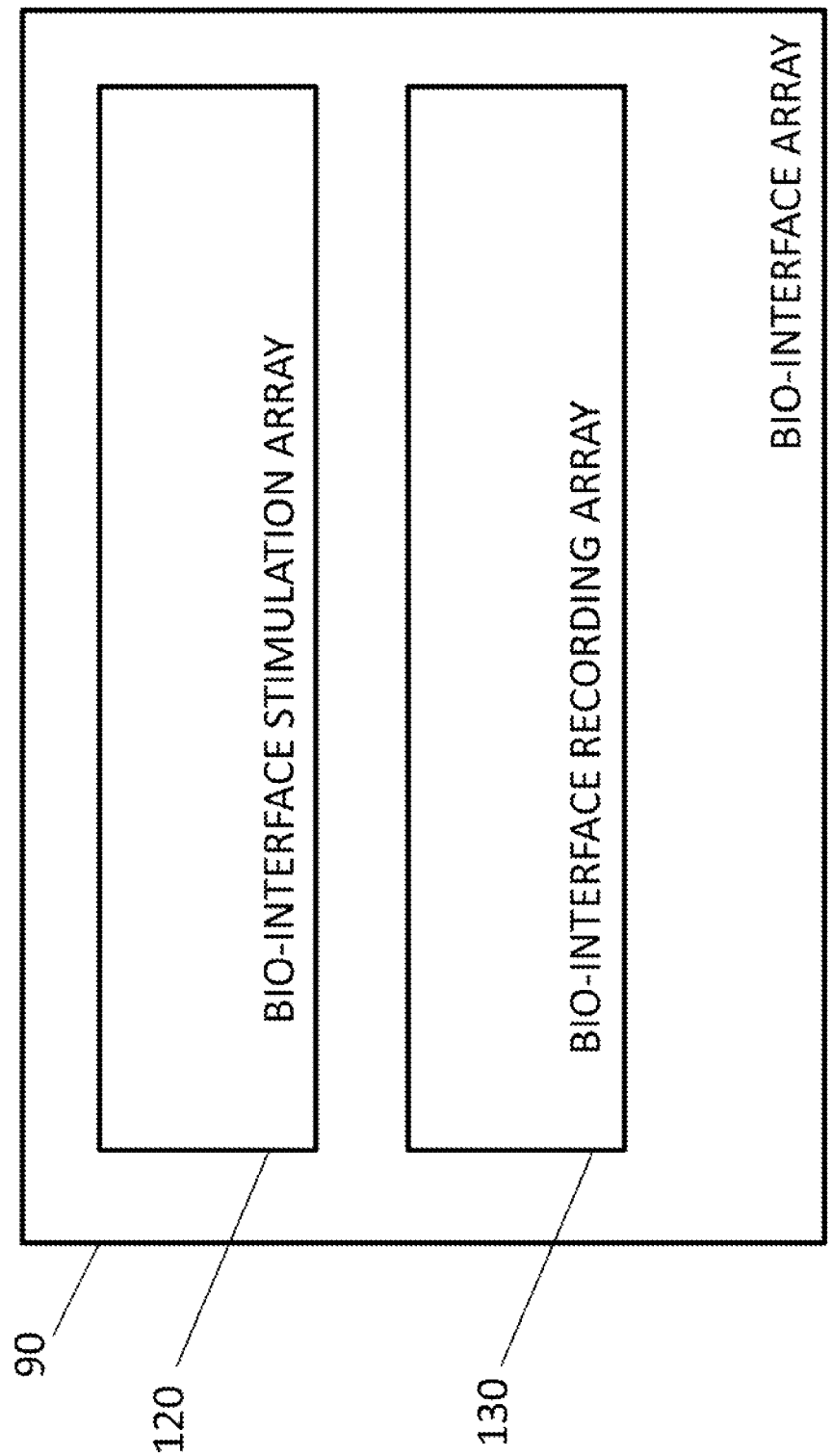
FIG. 2 is a block diagram showing bit rows of an illustrative bio-interface array according to an embodiment of the instant invention.
Figure 3:
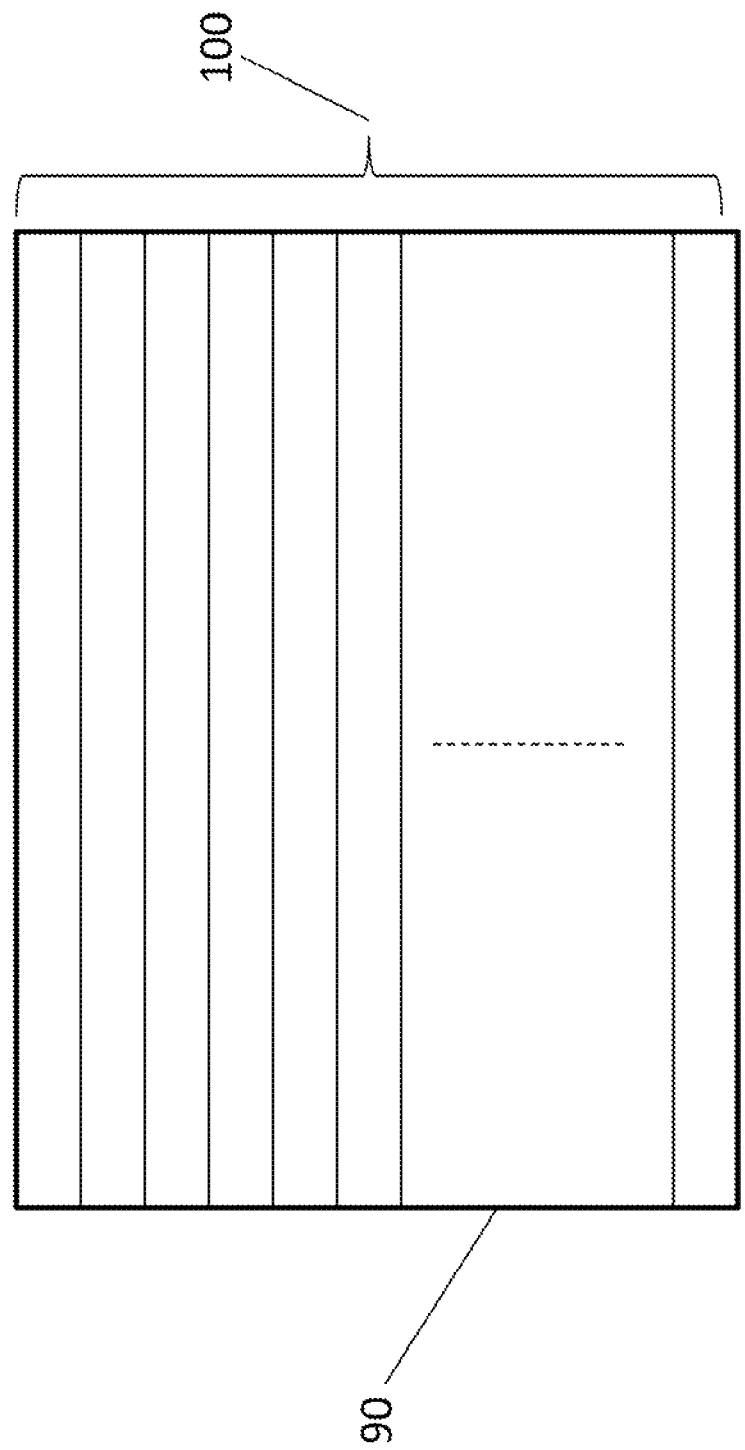
FIG. 3 is a block diagram of an illustrative embodiment of a bio-interface array according to the instant invention.

Shown by way of example in FIGS. 1-3, an embodiment of the invention includes an apparatus to drive an original analog signal 10 past a body wall 15 into a sensory tissue 20. The apparatus includes a standard analog-to-digital converter ("ADC") 30 converting an original analog signal 10 to a digital signal 40 at an analog-to-digital converter sample rate. An example of a standard ADC is the ADC within a Silabs F931. The apparatus includes a standard digital internal wireless transceiver 50 communicating wirelessly with the analog-to-digital converter 30 to receive the digital signal 40. Examples of such a standard digital transceiver 50 include a Bluetooth development module CSR CASIRA/BC4, CSR BC6, Texas Instruments CC8530, or Broadcom BCM4325. The ADC 30, for example, communicates via a wireless signal 41 with a standard digital transmitter or external wireless transceiver 45, which in turn wirelessly communicates with the standard digital transceiver 50. Examples of such a standard digital transmitter or transceiver include a Bluetooth development module CSR CASIRA/BC4, CSR BC6, Texas Instruments CC8530, or Broadcom BCM4325. The apparatus includes a standard digital data buffer 60 receiving the digital signal 51 from the digital transceiver 50. Examples of a digital data buffer 60 include standard random access memory in a standard microprocessor or microcontroller 140, standard flash memory in a digital transceiver, and a separate standard memory chip. The apparatus includes a standard digital-to-analog converter ("DAC") 70 communicating with the digital data buffer 60 and converting the digital signal 51 back into an reconstructed analog signal 71 which is the same as original analog signal 10, but at a digital-to-analog converter sample rate faster than the analog-to-digital converter 30 sample rate. The reconstructed analog signal 71 includes a plurality of intensity values. An example of a standard DAC is the one within the Silabs F931/921 family of microcontrollers, Maxim MX7821, or a standard small package DAC. The apparatus includes a standard pixel clock 80 matching the digital-to-analog converter sample rate. The apparatus includes a standard bio-interface array 90 comprising a plurality of electrodes and operably proximate to the sensory tissue 20, the bio-interface array 90 communicating with the digital-to-analog converter 70, the digital data buffer 60, and the pixel clock 80 so as to clock the plurality of intensity values in the original analog signal 10 from the digital-to-analog converter 70 into the plurality of electrodes of the bio-interface array 90. The pixel clock 80 may originate on the bio-interface array or the microprocessor and be sent to the bio-interface array.

Optionally, the apparatus further includes a standard row clock 110, wherein the bio-interface array 90 includes a plurality of bit rows 100, the bio-interface array 90 communicating with the row clock 110 so as to clock the plurality of intensity values in the original analog signal 10 from the digital-to-analog converter 70 and the digital data buffer 60 into the plurality of electrodes of the bio-interface array 90 by bit row. The row clock 110, for example, originates on the bio-interface array 90.

Optionally, the apparatus further includes a standard microprocessor 140 communicating with the pixel clock 80, the digital data buffer 60, and the bio-interface array 90 so as to controllably drive the reconstructed analog signal 71 into the sensory tissue 20. An example of a standard microprocessor 140 is a Silabs 8051 microcontroller found in a Silabs microprocessor board F931. Optionally, the original analog signal 10 further includes header data, such as a biphasic pulse, the microprocessor 140 controllably driving the original analog signal 10 into the sensory tissue 20 upon detection of the biphasic pulse.

Optionally, the bio-interface array 90 comprises at least one of a bio-interface stimulation array 120 and a bio-interface recording array 130, for example as shown in FIG. 2. The bio-interface stimulation array can be spatially separated from the bio-interface recording array or coincident with the bio-interface recording array.

Figure 4:
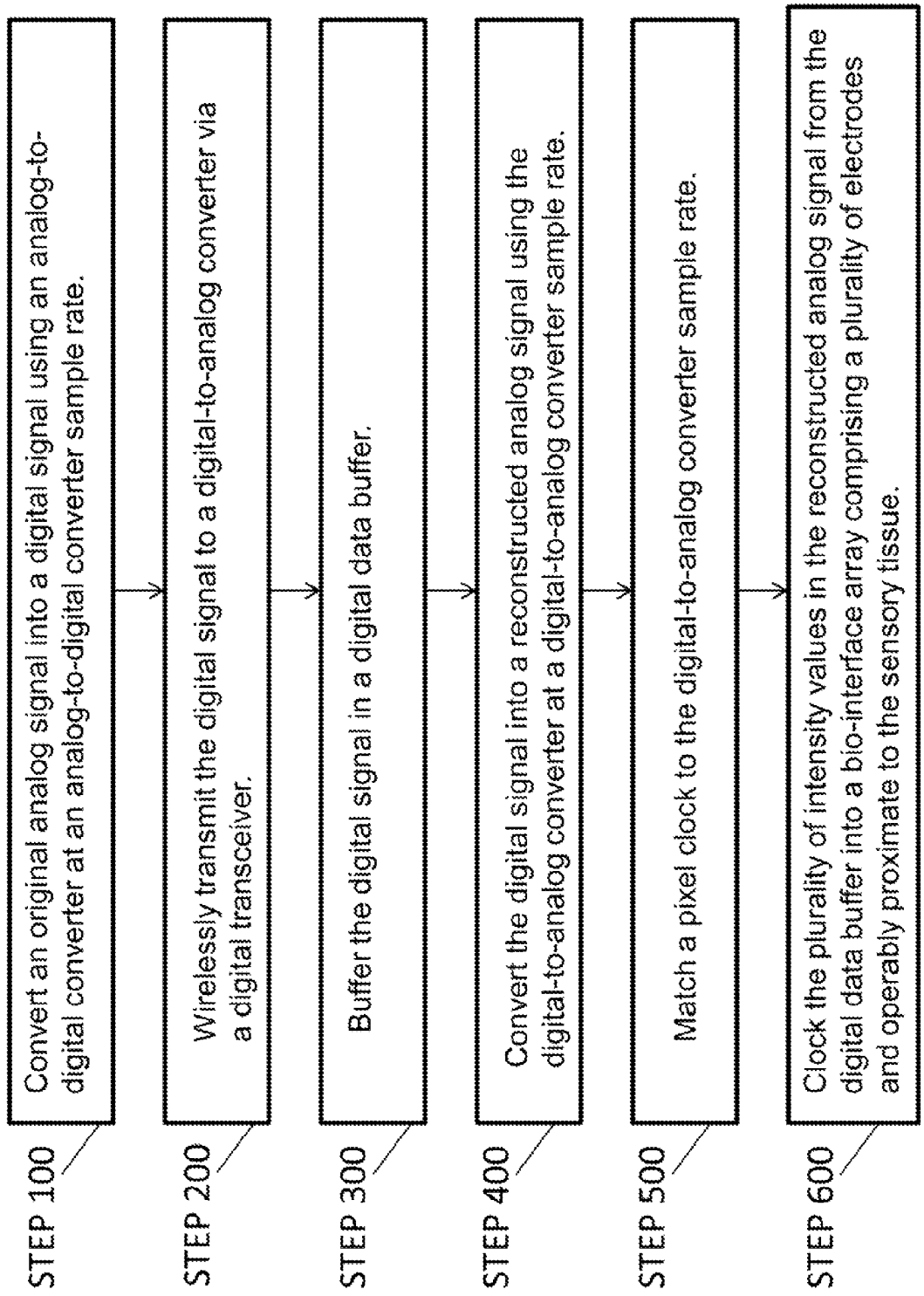
FIG. 4 is a flowchart of an illustrative method embodiment of the instant invention.

Shown by way of example in FIG. 4, an embodiment of the invention includes a method of driving an analog signal into a sensory tissue. In Step 100, an analog signal is converted into a digital signal using an analog-to-digital converter at an analog-to-digital converter sample rate. In Step 200, the digital signal is wirelessly transmitted to a digital-to-analog converter via a digital transceiver. In Step 300, the digital signal is buffered in a digital data buffer. In Step 400, the digital signal is converted into the analog signal using the digital-to-analog converter at a digital-to-analog converter sample rate faster than the analog-to-digital converter sample rate, the analog signal comprising a plurality of intensity values. In Step 500, a pixel clock is matched to the digital-to-analog converter sample rate. In Step 600, the plurality of intensity values in the analog signal from the digital data buffer is clocked into a bio-interface array comprising a plurality of electrodes and operably proximate to the sensory tissue.

Optionally, the bio-interface array comprises a plurality of bit rows, the bio-interface array communicating with a row clock. In Step 700, the plurality of intensity values in the analog signal is clocked from the digital-to-analog converter and the digital data buffer into the plurality of electrodes of the bio-interface array by bit row.

Optionally, in Step 800, the analog signal is controllably driven into the sensory tissue using a microprocessor communicating with the buffer, the pixel clock, and the bio-interface array. Optionally, the analog signal further comprises a biphasic pulse, the microprocessor controllably driving the analog signal into the sensory tissue upon detection of the biphasic pulse.

Optionally, the sensory tissue includes an eye, an ear, a prosthetic limb or electrically active tissue.

Optionally, the bio-interface array comprises a bio-interface stimulation array and/or a bio-interface recording array. The bio-interface stimulation array can be spatially separated from the bio-interface recording array or coincident with the bio-interface recording array.

An alternative embodiment of the invention includes a system for high speed wireless stimulation and biopotentials readout of a standard bio-interface device 90 in which chip controlling data is sent in addition to the stimulation data. A buffering method is used to accumulate data at low data rates and to release the buffered data at higher speeds. The control data is sent as bits in a "header" and separated from the bits to be converted to analog signals by a identifiable pattern of bits. The transmitted multiplexer timing data for the bio-interface array can be thus be removed from the video data stream based on identifying features. Data to control other chip functions such as the pixel clock rate, any row clock rate, whether to record bio-potentials and other desired functions.

In this example, the input analog video signal 10 enters the Analog-to-Digital convertor Silabs F931 30 and the digitized video signal 40 goes to a first Bluetooth development module CSR CASIRA/BC4 transmitter or transceiver. The digitized video signal 40 is wirelessly transmitted to the second Bluetooth development module 50. From there, the digitized video signal 40 is sent to the Silabs microprocessor board Silabs F931 140, buffered and converted back to an analog video signal 10, for example, at 1.4 MHz.

In this example, the digital data buffer 60 is, for example, the random access memory ("RAM") of the microprocessor 140 used to control the wireless chip and the bio-interface array 90. An illustrative RAM is in the Silabs 8051 microcontroller 140. The RAM buffer optionally exists on the wireless chip or on a separate extended RAM chip. The RAM size is ideally larger than the total data size of a single image (e.g., 3200 bytes for an illustrative 80×40 pixel bio-interface stimulation array) or larger than both an input image of stimulation intensities and the data of one or more recordings of the biopotentials via the recording array.

In this example, sensory tissue image data is received onto the Silabs 8051 board's microcontroller F931 chip via a standard Universal Asynchronous Receiver/Transmitter ("UART") although the data entry can be through a different connection, such as a Serial Peripheral Interface ("SPI") Bus. For example, the UART from the wireless chip to the microcontroller 140 is operated at 230400 bits per second. As an example, any complete UART bytes are stored into an indexed variable. When, for example, 3200 bytes (e.g., one image frame worth of data) are stored, the microcontroller software (for example, as discussed in the COMPUTER PROGRAM LISTING APPENDIX below) holds the data, until the programmed reset pulse timer triggered an interrupt to release the data. For example, the 8 bit image data is then converted to analog data using a 6-bit current DAC, one 80 pixel row at a time. For example, the DAC takes 719 ns to convert one pixel from analog to digital; this can match an analog multiplexer pixel clock 80 of 1.4 MHz. In this example, the effective analog data rate is 686 times faster after buffering. This allows for the output data to match a fast analog multiplexer clock.

In this example, the 80 pixels of analog output for each row are separated by a dc level. The image frame rate is, for example, approximately 7 frames per second. A frame of data is released in a burst triggered internally on the microcontroller 140 by a programmed frame reset pulse. The inset shows the 7 bursts occurring in 1 second. The trace in FIG. 4b shows the leading edge of the image frame. Here one can see the digitized levels of the output image data.

In this example, the controlling header data is interpreted by the microcontroller 140 and the following data is sent to the buffer 60 or the data word input of the stimulation chip 90 to manage chip timing.

In this example, the analog demultiplexer, for example, has capacitors to store the individual pixel values until a desired release time. A separate output multiplexer can read out signals from the pixels. The output signals may be voltage samples, for example, from the biological implantation site. An analog to digital convertor digitizes the data at high data rates. A buffer 60 is used to store the digitized data for transmission at slower rates. The output signals can be sent raw or processed to reduce the amount of data. The processing may involve neuronal or cardiac spike detection.

Another embodiment of the instant invention involves a data source (such as a standard camera) that is directly wired to the stimulation array but wherein the data is processed externally. In this embodiment, the image data is buffered and wirelessly transmitted out at a slower clock, processed and then retransmitted wirelessly at the slow data clock. The data is the buffered prior to demultiplexing by the stimulation array. The data buffering is perform in the same manner as the examples above.

Figure 5:
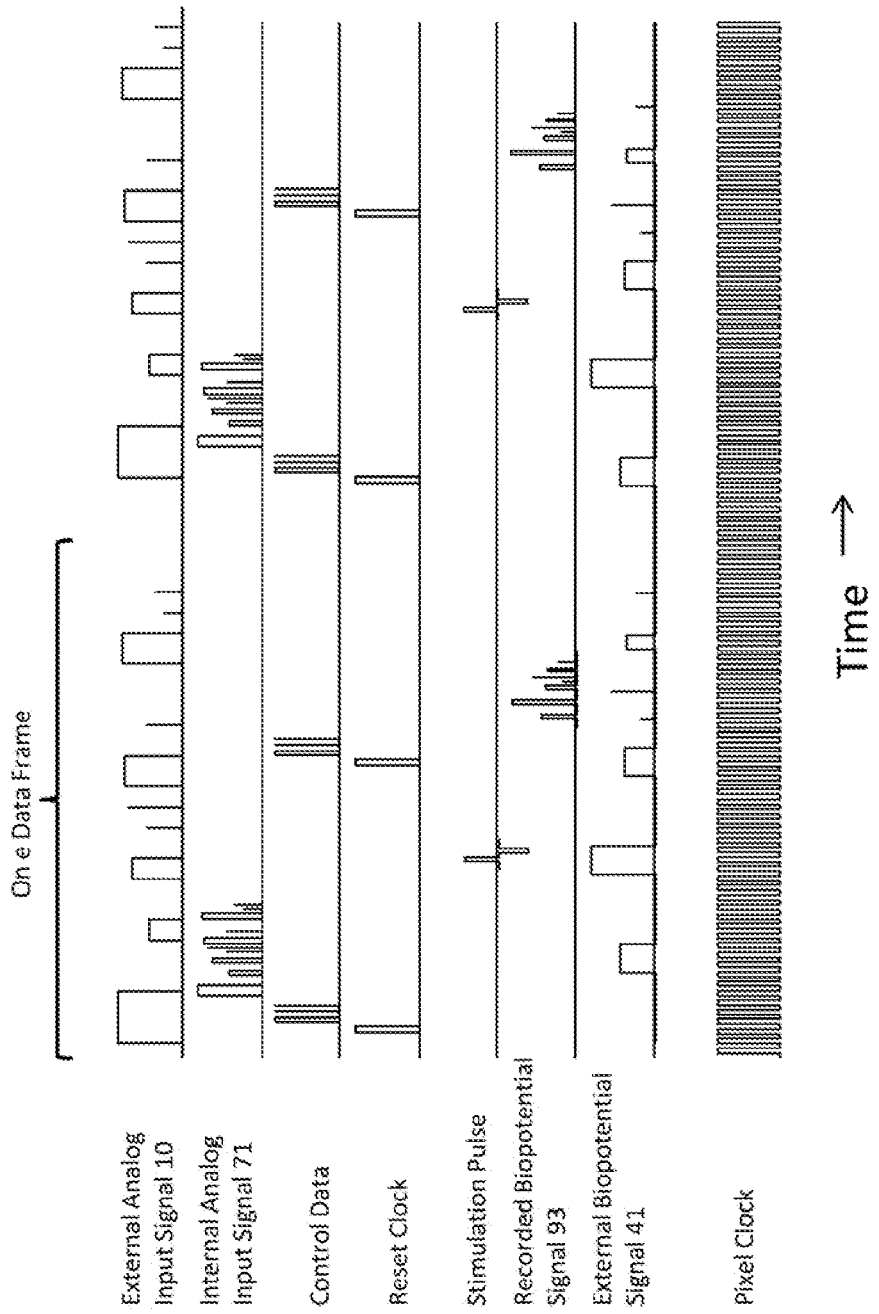
FIG. 5 is an illustrative timing diagram for a bio-interface stimulation array according to an embodiment of the instant invention.

FIG. 5 shows a generalized and illustrative schematic of the NRL stimulation array timing. The Reset Clock pulse stalls a frame. The Control represents the digital instructions for a frame. The internal analog input signal 71 contains the intensities that the stimulation array will drive into the biological tissue. The time duration of the internal analog input signal is much less than the time between two frame reset pulses. It is also less than the duration of the original external original analog signal 10. The internal analog data is operating at 1 Mhz in this example. The multiplexer loads the pixels in 0.9696 milliseconds. Then the biphasic stimulation pulse can be applied to drive the image pattern into the biological tissue. Since the pixel data is loaded quickly, the biphasic pulse can have a duration longer than the time it takes to load one pixel. In this example, the data buffering would allow the wireless data to be transmitted with a data clock of less than 0.6 MHz (21 frames/second*3200 pixels/frame*8 bits/pixel) but drive a 1 Mhz output. The second reset clock pulse and control data pulses may setup a recording of the external biopotentials. In this case the recorded biopotentials signal 93 is acquired at 1 Mhz and then the buffer 60 can be used to store and transmit the digitized data (143 and 41) at a slower rate.

The many features and advantages of the invention are apparent from the detailed specification, and thus, it is intended by the appended claims to cover all such features and advantages of the invention which fall within the true scope and spirit of the invention. Further, because numerous modifications and variations will readily occur to those skilled in the art, it is not desired to limit the invention to the exact construction and operation as illustrated and described, and accordingly, all suitable modifications and equivalents may be resorted to, falling within the scope of the invention.

COMPUTER PROGRAM LISTING APPENDIX

An example of buffering code on the Silabs microcontroller for use in accordance with one or more embodiments of the instant invention is as follows.

```
INTERRUPT(PCA0_ISR, INTERRUPT_PCA0)
{
unsigned long k;
int ii;
if (CCF0)                // If Module 0 caused the interrupt
{
            // Clear module 0 interrupt flag.
```

```
        //BIPHASE1 = 0;
        //BIPHASE1 = 1;
        CCF0 = 0;
        //LED = !LED;
// Set up the variable for the following edge
//Next_Compare_Value = PCA0CP1 + DIVIDE_RATIO;
}
if (CCF1)                    // If Module 0 caused the interrupt
{
        CCF1 = 0;            // Clear module 0 interrupt flag.
PCA0CPL1 = (Next_Compare_Value & 0x00FF);
PCA0CPH1 = (Next_Compare_Value & 0xFF00)>>8;
        FRAMEDELAY++;
        if (FRAMEDELAY == 25)
        {
        RESET1 = 0;
        RESET1 = 0;
        RESET1 = 1;
        PDATA1 = 0;
        PDATA1 = 0;
        PDATA1 = 0;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 1;
        PDATA1 = 0;
        PDATA1 = 1;
        PDATA1 = 0;
        PDATA1 = 1;
        PDATA1 = 1;
        PDATA1 = 1;
        PDATA1 = 0;
        PDATA1 = 0;
        PDATA1 = 0;
        PDATA1 = 1;
        RESET1 = 1;
        if (UART_full == 1)
        {
        k=(UART_BUFFERSIZE)-1;
                while ( k > 0)
                {
                //LED = 0;
                IREF0CN = UART_Buffer[k];
                IREF0CN = UART_Buffer[k-1];
                IREF0CN = UART_Buffer[k-2];
                IREF0CN = UART_Buffer[k-3];
                IREF0CN = UART_Buffer[k-4];
                IREF0CN = UART_Buffer[k-5];
                IREF0CN = UART_Buffer[k-6];
                IREF0CN = UART_Buffer[k-7];
                IREF0CN = UART_Buffer[k-8];
                IREF0CN = UART_Buffer[k-9];
                IREF0CN = UART_Buffer[k-10];
                IREF0CN = UART_Buffer[k-11];
                IREF0CN = UART_Buffer[k-12];
                IREF0CN = UART_Buffer[k-13];
                IREF0CN = UART_Buffer[k-14];
                IREF0CN = UART_Buffer[k-15];
                IREF0CN = UART_Buffer[k-16];
                IREF0CN = UART_Buffer[k-17];
                IREF0CN = UART_Buffer[k-18];
                IREF0CN = UART_Buffer[k-19];
                IREF0CN = UART_Buffer[k-20];
                IREF0CN = UART_Buffer[k-21];
                IREF0CN = UART_Buffer[k-22];
                IREF0CN = UART_Buffer[k-23];
                IREF0CN = UART_Buffer[k-24];
                IREF0CN = UART_Buffer[k-25];
                IREF0CN = UART_Buffer[k-26];
                IREF0CN = UART_Buffer[k-27];
                IREF0CN = UART_Buffer[k-28];
                IREF0CN = UART_Buffer[k-29];
                IREF0CN = UART_Buffer[k-30];
                IREF0CN = UART_Buffer[k-31];
                IREF0CN = UART_Buffer[k-32];
                IREF0CN = UART_Buffer[k-33];
                IREF0CN = UART_Buffer[k-34];
                IREF0CN = UART_Buffer[k-35];
                IREF0CN = UART_Buffer[k-36];
                IREF0CN = UART_Buffer[k-37];
                IREF0CN = UART_Buffer[k-38];
                IREF0CN = UART_Buffer[k-39];
                IREF0CN = UART_Buffer[k-40];
                IREF0CN = UART_Buffer[k-41];
                IREF0CN = UART_Buffer[k-42];
                IREF0CN = UART_Buffer[k-43];
                IREF0CN = UART_Buffer[k-44];
                IREF0CN = UART_Buffer[k-45];
                IREF0CN = UART_Buffer[k-46];
                IREF0CN = UART_Buffer[k-47];
                IREF0CN = UART_Buffer[k-48];
                IREF0CN = UART_Buffer[k-49];
                IREF0CN = UART_Buffer[k-50];
                IREF0CN = UART_Buffer[k-51];
                IREF0CN = UART_Buffer[k-52];
                IREF0CN = UART_Buffer[k-53];
                IREF0CN = UART_Buffer[k-54];
                IREF0CN = UART_Buffer[k-55];
                IREF0CN = UART_Buffer[k-56];
                IREF0CN = UART_Buffer[k-57];
                IREF0CN = UART_Buffer[k-58];
                IREF0CN = UART_Buffer[k-59];
                IREF0CN = UART_Buffer[k-60];
                IREF0CN = UART_Buffer[k-61];
                IREF0CN = UART_Buffer[k-62];
                IREF0CN = UART_Buffer[k-63];
                IREF0CN = UART_Buffer[k-64];
                IREF0CN = UART_Buffer[k-65];
                IREF0CN = UART_Buffer[k-66];
                IREF0CN = UART_Buffer[k-67];
                IREF0CN = UART_Buffer[k-68];
                IREF0CN = UART_Buffer[k-69];
                IREF0CN = UART_Buffer[k-70];
                IREF0CN = UART_Buffer[k-71];
                IREF0CN = UART_Buffer[k-72];
                IREF0CN = UART_Buffer[k-73];
                IREF0CN = UART_Buffer[k-74];
                IREF0CN = UART_Buffer[k-75];
                IREF0CN = UART_Buffer[k-76];
                IREF0CN = UART_Buffer[k-77];
                IREF0CN = UART_Buffer[k-78];
                IREF0CN = UART_Buffer[k-79];
                //OUT1 = 1;
                k=k-80;
                //LED =.5;
                }
        UART_Buffer_Size =              // reset the array size to 0
        UART_BUFFERSIZE:
                UART_Input_First =      // reset the counter
                UART_BUFFERSIZE;
        IREF0CN = 0x40 ;
                UART_full = 0;   //say UART is empty
        }
                FRAMEDELAY = 0;
        }
        LED = 1;
        LED = 0;
// Set up the variable for the following edge
```

-continued

```
    Next_Compare_Value = PCA0CP1 + DIVIDE_RATIO;
   }
   else            // Interrupt was caused by other bits.
   {
      //LED = !LED;          // Invert the LED pin
      PCA0CN &= ~0x86;       // Clear other interrupt flags for PCA
   //PCA0L = 0xF8;
   //PCA0H = 0xFF;
      //PCA0=0xFFFE;
      }
}
```

What is claimed as new and desired to be protected by Letters Patent of the United States is:

1. An apparatus to drive an analog signal into a sensory tissue comprising:
   an analog-to-digital converter converting an original analog signal to a digital signal at an analog-to-digital converter sample rate;
   a digital transceiver communicating wirelessly with said analog-to-digital converter to receive the digital signal;
   a digital data buffer receiving the digital signal from said digital transceiver
   a digital-to-analog converter communicating with said digital data buffer and converting the digital signal into a reconstructed analog signal at a digital-to-analog converter sample rate faster than the analog-to-digital converter sample rate, the reconstructed analog signal comprising a plurality of intensity values;
   a pixel clock matching the digital-to-analog converter sample rate;
   a bio-interface array comprising a plurality of electrodes and operably proximate to the sensory tissue, said bio-interface array communicating with said digital-to-analog converter, said digital data buffer, and said pixel clock so as to clock the plurality of intensity values in the reconstructed analog signal from the digital-to-analog converter into the plurality of electrodes of the bio-interface array.

2. The apparatus according to claim 1, further comprising a row clock, wherein said bio-interface array comprises a plurality of bit rows, said bio-interface array communicating with said row clock so as to clock the plurality of intensity values in the reconstructed analog signal from said digital-to-analog converter and said digital data buffer into the plurality of electrodes of said bio-interface array by bit row.

3. The apparatus according to claim 1, further comprising a microprocessor communicating with said pixel clock, said digital data buffer, and said bio-interface array so as to controllably drive the reconstructed analog signal into the sensory tissue.

4. The apparatus according to claim 3, wherein the analog signal further comprises a biphasic pulse, said microprocessor controllably driving the reconstructed analog signal into the sensory tissue upon detection of the biphasic pulse.

5. The apparatus according to claim 1, wherein said bio-interface array comprises at least one of a bio-interface stimulation array and a bio-interface recording array.

6. The apparatus according to claim 5, wherein the bio-interface stimulation array is one of spatially separated from the bio-interface recording array and coincident with the bio-interface recording array.

7. A method of driving an analog signal into a sensory tissue comprising:
   converting an original analog signal into a digital signal using an analog-to-digital converter at an analog-to-digital converter sample rate;
   wirelessly transmitting the digital signal to a digital-to-analog converter via a digital transceiver;
   buffering the digital signal in a digital data buffer;
   converting the digital signal into a reconstructed analog signal using the digital-to-analog converter at a digital-to-analog converter sample rate faster than the analog-to-digital converter sample rate, the reconstructed analog signal comprising a plurality of intensity values;
   matching a pixel clock to the digital-to-analog converter sample rate; and
   clocking the plurality of intensity values in the reconstructed analog signal from the digital data buffer into a bio-interface array comprising a plurality of electrodes and operably proximate to the sensory tissue.

8. The method according to claim 7, further comprising controllably driving the reconstructed analog signal into the sensory tissue using a microprocessor communicating with the buffer, the pixel clock, and the bio-interface array.

9. The method according to claim 8, wherein the analog signal further comprises a biphasic pulse, the microprocessor controllably driving the reconstructed analog signal into the sensory tissue upon detection of the biphasic pulse.

10. The method according to claim 7, wherein the sensory tissue comprises one of an eye, an ear, and a prosthetic limb.

11. The method according to claim 7, wherein said bio-interface array comprises at least one of a bio-interface stimulation array and a bio-interface recording array.

12. The method according to claim 11, wherein the bio-interface stimulation array is one of spatially separated from the bio-interface recording array and coincident with the bio-interface recording array.

13. The method according to claim 7, wherein the bio-interface array comprises a plurality of bit rows, the bio-interface array communicating with a row clock, wherein the method further comprises clocking the plurality of intensity values in the reconstructed analog signal from the digital-to-analog converter and the digital data buffer into the plurality of electrodes of the bio-interface array by bit row.

* * * * *